United States Patent [19]

Reimers

[11] 4,230,453
[45] Oct. 28, 1980

[54] LIGHT ASSEMBLY FOR USE WITH A DENTAL HANDPIECE

[75] Inventor: Robert Reimers, Gardner, Kans.

[73] Assignee: Litton Industrial Products Inc., Beverly Hills, Calif.

[21] Appl. No.: 29,236

[22] Filed: Apr. 11, 1979

[51] Int. Cl.³ .............................................. A61C 1/00
[52] U.S. Cl. ..................................... 433/29; 433/115; 408/16; 362/119
[58] Field of Search ..................... 433/29, 115; 128/23; 408/16; 362/119, 120, 115, 804

[56] References Cited

U.S. PATENT DOCUMENTS

| 2,038,911 | 4/1936 | Stutz et al. | 433/29 |
| 2,539,828 | 1/1951 | Goldis et al. | 433/29 |
| 3,889,661 | 6/1975 | Fiore | 362/120 |
| 4,020,556 | 5/1977 | Sotman | 433/29 |

FOREIGN PATENT DOCUMENTS

| 1065566 | 9/1959 | Fed. Rep. of Germany | 433/29 |
| 1068425 | 11/1959 | Fed. Rep. of Germany | 433/29 |
| 1466959 | 2/1969 | Fed. Rep. of Germany | 433/29 |

Primary Examiner—Louis G. Mancene
Assistant Examiner—John J. Wilson
Attorney, Agent, or Firm—Robert A. Seldon

[57] ABSTRACT

The assembly includes an electrically insulative support member which overlies electrical contacts on the handpiece and further includes a pair of contact members which press a flexible printed circuit against the electrical contacts to couple a pair of bulbs to the electrical power source. The light source assembly additionally includes means for effectively sealing the contact regions from environmental fluids.

5 Claims, 7 Drawing Figures

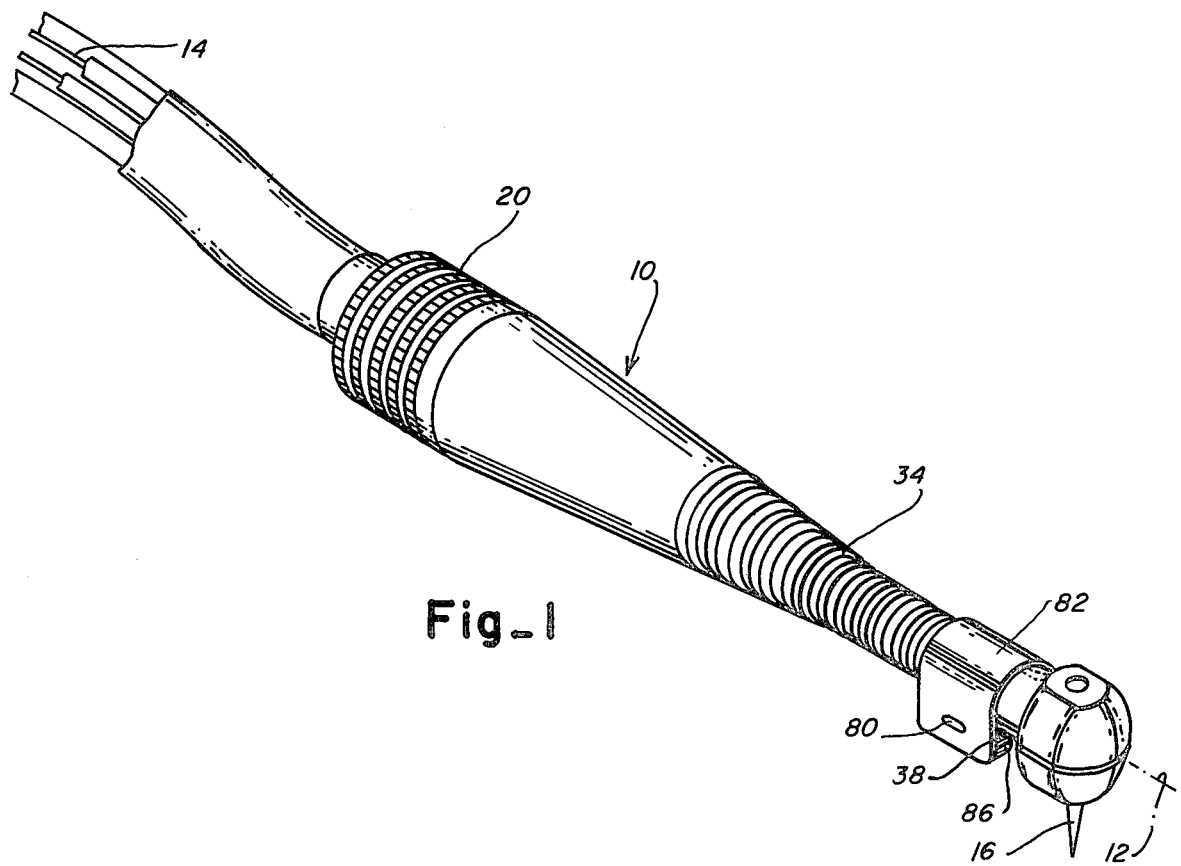
Fig_1

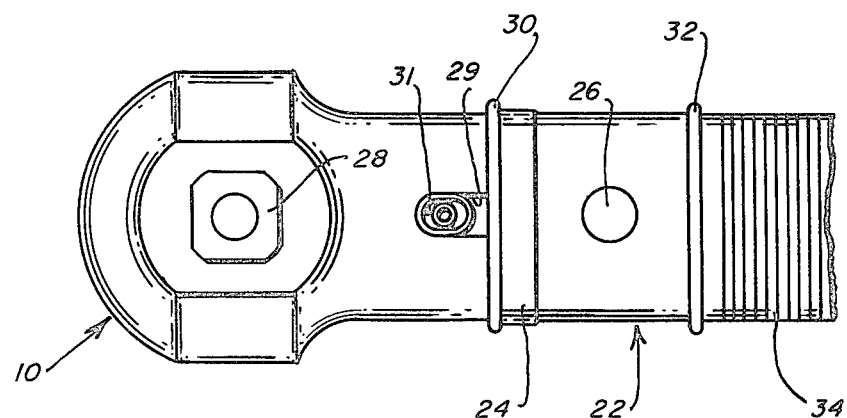
Fig_2
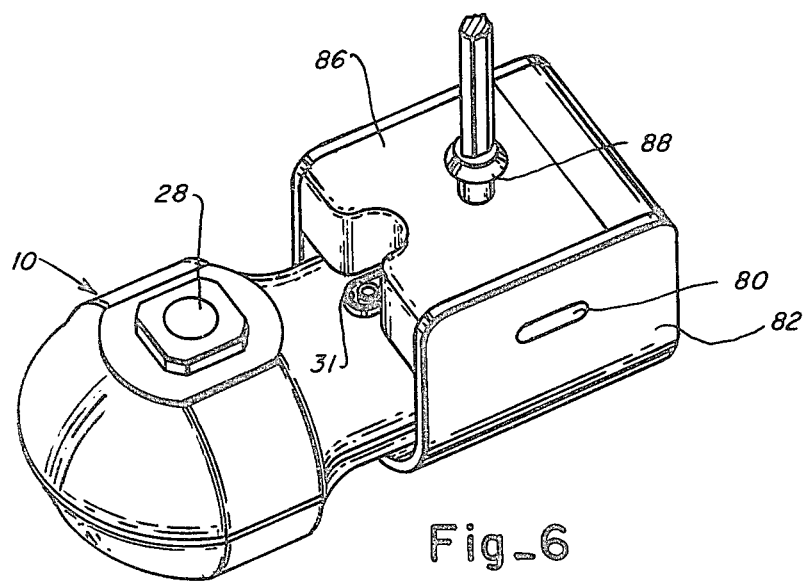
Fig_6

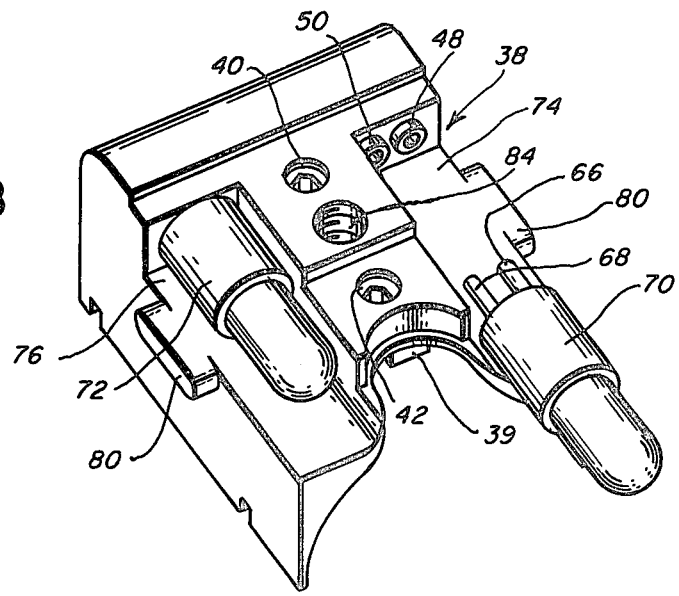
Fig._3B
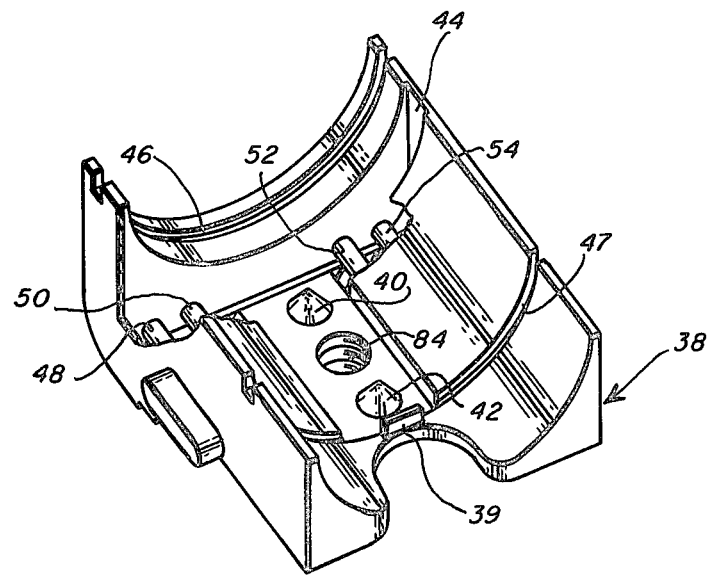
Fig._3A
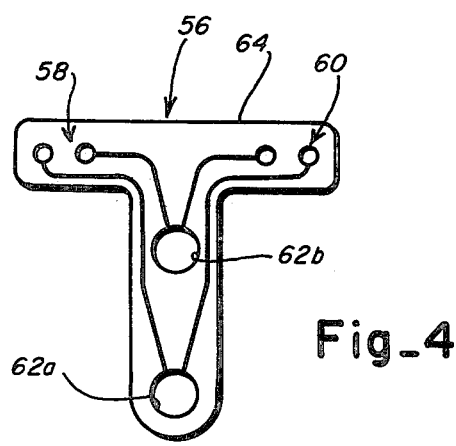
Fig._4

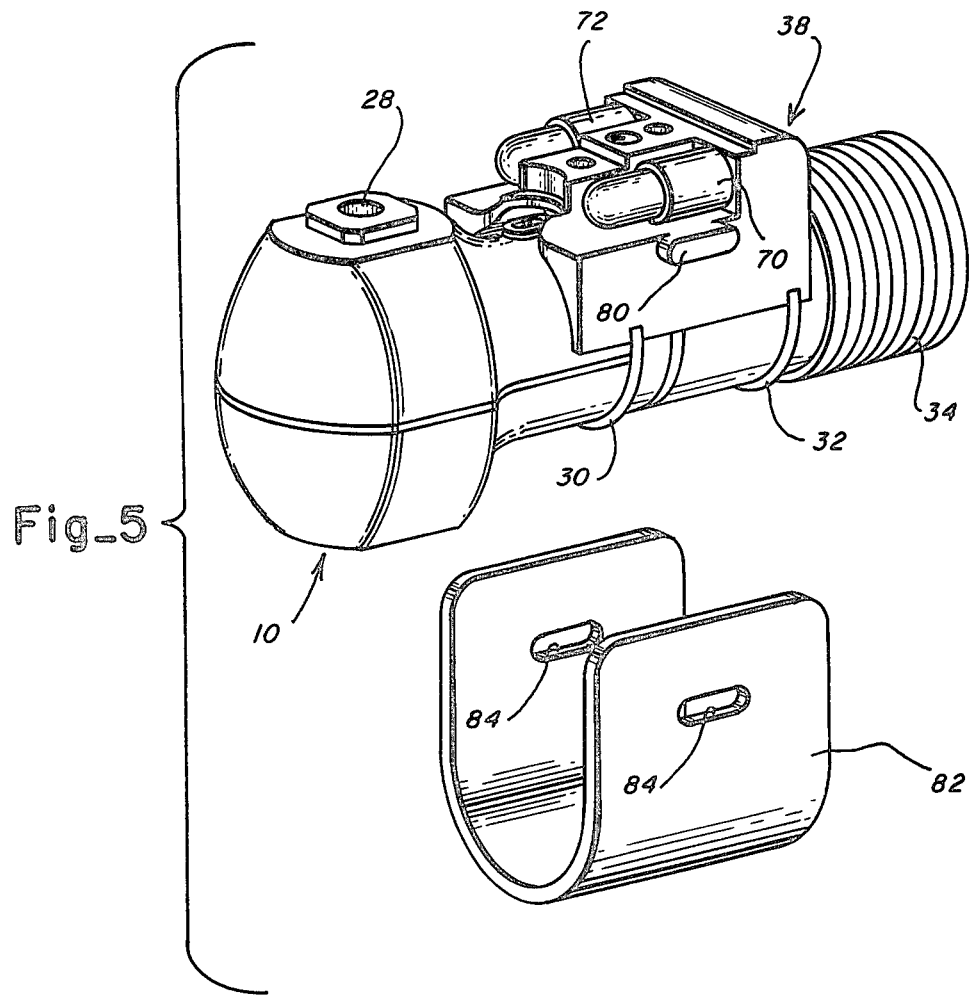

LIGHT ASSEMBLY FOR USE WITH A DENTAL HANDPIECE

FIELD OF THE INVENTION

The present invention relates to dentistry and, more particularly, to a light source for use with a dental handpiece.

The use of such light sources to illuminate a patient's mouth is highly desirable. Conventionally, light is directed into the patient's mouth by means of an overhead lamp, the rays from which are deflected by a hand-held mirror. The inconvenience of such an arrangement is apparent to those skilled in the art, and it is highly desirable to eliminate the need for the dentist or dental technician to hold a mirror while manipulating the dental instrument with the other hand.

Accordingly, a light source assembly which attaches to the dental handpiece without impeding the dentist's vision is provided herein. The design provides for the non-destructible replacement of the light bulbs, and for the replacement of such bulbs without the necessity of removing the assembly from the handpiece. Additionally, the light source assembly is adapted for use with autoclavable handpieces whereby the source need not be removed from the handpiece during the sterilization process. The last main feature is particularly important since there are many instances in which the light source assembly will be within the patient's mouth during gum cutting and other surgical operations. Consequently, the assembly will not provide a source of bacteria which could lead to infections.

As is known in the art, dental handpieces are generally elongated members which include first connecting means at a proximal end for coupling the handpiece to a source of air or water and can be used to couple the handpiece to electrical power, and further include a second connecting means generally axially spaced therefrom at its distal end for coupling the handpiece to a dental work tool. The work tool may, for example, be a dental drill when the handpiece is a drill handpiece or, alternatively, a scaler tip when the handpiece is a scaler handpiece. In either case, the handpiece includes an electrical conductor for electrically coupling the first connecting means to an exterior contact region adjacent the distal portion of the handpiece.

SUMMARY OF THE INVENTION

The improved light source assembly described herein comprises an electrically insulative support member which is adapted to overlie the contact region of the handpiece. A pair of electrically conductive contact members protrude from the radially inward surface of the support member; that is to say, the surface which is proximate to the handpiece. The contact members thereby contact the contact region when the support member is mounted on the handpiece. At least one bulb is mounted on the radially outward surface of the support member. The bulb includes first and second electrical leads.

A flexible printed circuit for coupling one of the contact members to respective first bulb leads and for coupling the other contact member to respective second bulb leads is also included.

In accordance with one aspect of the invention, means are provided for effectively sealing the contact region and contact members from environmental fluids. These environmental fluids are typically saliva, fluids used by the dentist in the oral cavity and autoclave fluids, all of which would otherwise detrimentally effect the connection between the handpiece and the light assembly. A lens cover serves to seal the bulb and the electrical connections thereto from the environmental fluids.

In accordance with the second aspect of the invention, the flexible printed circuit includes a pair of through-holes which are securely coupled to respective receptacle members formed within the support member to freely accept the first and second leads from the bulb. The bulbs may accordingly be replaced without the need for any cutting, soldering or other connection-breaking operation except for the pulling of the bulb from the receptacles.

In accordance with a third aspect of the invention, the light assembly includes electrical connection means which do not expose the patient to hazards related to contact with the lamp voltage.

Other advantages, features and construction details may be appreciated by reference to the following description of the preferred embodiment, which is to be read in conjunction with the following drawings forming a part thereof.

BRIEF DESCRIPTION OF THE DRAWINGS

FIG. 1 is a perspective view of a light source assembly constructed in accordance with the invention and mounted on a dental handpiece, FIG. 2 is an enlarged fragmentary perspective view showing the portion of the handpiece adjacent the distal end and the electrical contact region thereon, FIGS. 3A and 3B are respectively top and bottom perspective views showing the support member of the light source assembly, FIG. 4 illustrates a flexible printed circuit used in the light source assembly, FIG. 5 is an enlarged fragmentary perspective view showing the light source assembly mounted on the handpiece.

DESCRIPTION OF THE PREFERRED EMBODIMENT

Initial reference is made to FIG. 1, which is a perspective view of a light source assembly mounted on a dental handpiece. The illustrated handpiece 10 is adapted for use as a dental drill, although it will be understood that the present invention may be used with any dental handpiece such as that employed as part of a dental scaler. The handpiece is shown to have an elongated form disposed about a central axis 12 and comprising a first connecting means 20 at its proximal end for coupling the handpiece to a source of electrical power via an electrical lead 14.

The handpiece 10 additionally includes second connection means generally axially spaced from the first connecting means at the distal end for coupling the handpiece to a dental work tool 16. In the illustrated embodiment, the tool 16 is a drill bit.

FIG. 2 is an enlarged perspective view showing the portion of the handpiece adjacent the distal end and, more specifically, and electrical contact region 22. The contact region includes an electrically conductive ring 24 circumferentially positioned on the exterior surface of the handpiece 10, and an electrically conductive ground connection spot 26 axially spaced therefrom. The conductive ring 24 is coupled to the first connecting means 20 via an electrical conductor which runs axially along the interior of the handpiece. The spot 26 is electrically coupled to the handpiece which acts as ground via an appropriate connection to the power source through the coupling means 20.

Also visible in FIG. 2 is the second connecting means 28 by which the handpiece 10 is coupled to the drill bit 16 in any manner know in the art, and a generally U-shaped cavity 29 through which an air nozzle 31 maintains the work area free from dental debris.

In accordance with the invention, a pair of O-rings 30, 32 are positioned on the handpiece. The O-ring 30 is positioned on the forward edge of the electrical contact ring 24; the surface of the contact ring 24 is elevated slightly from the handpiece surface so that the ring 24 edge forms a stop with respect to the O-ring 30. The other O-ring 32 is positioned just forward of the corrugated gripping surface 34 of the handpiece body. As will be apparent herein below, the O-rings serve to effectively seal the contact region from such environmental fluids as saliva, autoclave fluids, fluids used by the dentist in the oral cavity and by providing a resilient surface interjacent the handpiece and the hereinafter described support member of the light source assembly.

The support member and related components of the light source assembly are best described with reference to FIGS. 3A and 3B which are respectively perspective top and bottom views of the support member 38. The support member 38 is formed from an electrically insulative material such as polysulfone plastic and is adapted to overlie the contact region 22 of the handpiece 10. The top and bottom surfaces of the support member 38 may be referred to, respectively, as the radially outward and radially inward surfaces, since they have the relative relationship with respect to the central axis of the handpiece when the light assembly is mounted thereon.

As shown in FIG. 3A, the support member 38 includes a radially inwardly extending finger 39 adapted to extend into the cavity 29 (FIG. 2) without blocking the air flow from the nozzle 31. A pair of contact members 40, 42 protrude from the bottom surface of the support member. As will be explained below, the contact members 40, 42 serve to press a flexible printed circuit into contact with the ground terminal 26 and the contact ring 24 of the contact region 22 (FIG. 2) when the support member is mounted on the handpiece. The bottom surface of the support member 38 additionally includes a laterally extending first groove 44 at its rearward, or proximate, end and a second O-ring-accepting groove 46 at the proximal end. A portion of four electrically conductive receptacle members 48, 50, 52, 54 may be seen passing through the walls of the first groove 44 so as to be exposed within the groove.

In accordance with the invention, electrical coupling between the handpiece and light source assembly is provided by means of a flexible printed circuit shown in FIG. 4. The illustrated flexible printed circuit 56 is a generally T-shaped circuit having first and second through-hole pairs 58, 60 and a pair of electrically conductive pads 62a, b. Electrically conductive circuit paths couple a selected one of the pads 62a, b to respective selected ones of the hole pair 58, 60. The flexible circuit is then mounted on the bottom surface of the member 38 with edge 64 inserted into the channel 44. The receptacles 48, 50, 52, 54 are respectively inserted through the hole pairs 56, 60 during construction of the light assembly; the pads 62a, b are positioned on the printed circuit 56 to overlie the contact ring 24 and contact spot 26, and are firmly pressed against these members by the contact members 40, 42.

As shown in FIG. 3A, the receptacles accomodate the electrical leads of a pair of axially oriented bulbs 70, 72. For example, the receptacles 48, 50 respectively accomodate the leads 66, 68 of the bulb 70 which is illustrated in a partially withdrawn position for clarity. The bulbs 70, 72 are positioned within axially extending channels 74, 76 formed in the surface of the support member 38. It will be appreciated that the bulbs may be easily replaced since they may be disconnected by simply pulling them from the receptacles.

As shown in FIG. 5, the supporting member 38 is mounted onto the handpiece 10 so that the O-rings 30, 32 fit into the grooves 47, 46 with the O-ring 30 remaining on the leading edge of the contact ring 24. The finger 39 (FIG. 3A) extends into the cavity 29 (FIG. 2) to prevent rotation of the light assembly.

A stiff but springy generally U-shaped clip 82, formed from a corrosion-resistive material such as beryllium copper, is positioned on the opposite side of the handpiece from the support member 38 and slid over the handpiece. The legs of the clip 82 are spread by lateral projections 80 of the support member 38 as the clip 82 is pressed onto the handpiece. The clip 82 is locked onto the handpiece when the lateral projections 80 engage respective openings 84 in the legs of the clip 82.

The set screws forming the contact members 40, 42 are tightened into threaded holes in the radially outward surface of the support member. Because the pads 62a, b are on the radially inward side of the printed circuit, while the contact members 40, 42 press against the radially outward side, the contact members do not represent shock hazards to the patient. For additional protection, the contact members may be formed from electrically insulative material.

Finally, with reference to FIG. 6, a lens cap 86 is placed over the supporting member and is secured by means of a screw 88 which is aligned with a threaded screw hole 84 (FIG. 3A) formed in the support member interjacent the two contact members 40, 42. The lens cover protects the bulbs and, additionally, provides a degree of safety by preventing particles such as glass from broken bulbs from entering the patient's mouth.

It will be appreciated from the foregoing description that the present invention provides easily removable bulbs which are merely slid in and out of the receptacles. The clip 82 seals the unit against the O-rings to provide sealing of the electrical contacts from autoclave fluids, thereby additionally maintaining the integrity of the autoclave fluid. It will additionally be appreciated that the two screws forming the contact members 40, 42 may alternatively pass through the support member 38 and press the flexible circuit 64 against the contact ring and handpiece body. In either embodiment, the tightening action of the screws provide additional sealing pressure and prevent rotation of the light assembly on the handpiece during use.

While the foregoing description has been directed to a preferred embodiment of the present invention, it will be understood that many variations and modifications are obvious to those skilled in the art. Accordingly, it is intended that the appended claims be construed as broadly as permissible, in light of the prior art, and that such variations and modifications be included as within the spirit and scope of the invention.

We claim:

1. For use with an elongated dental handpiece having first connecting means at its proximal end for coupling the handpiece to a source of electrical power and having second connecting means generally axially spaced therefrom at its distal end for coupling the handpiece to a dental work tool and including an electrical conductor for electrically coupling the first connecting means to an exterior contact region adjacent the distal portion of the handpiece, an improved light source assembly comprising:

an electrically insulative support member adapted to overlie the contact region of the handpiece, a pair of electrically conductive contact members protruding from the radially inward surface of the support member which is proximate to the handpiece so as to contact the contact region thereof, at least one bulb mounted on the radially outward surface of the support member and including first and second electrical leads, first and second receptacle members formed within the support member to respectively freely accept the first and second leads from the bulb a flexible printed circuit for securely coupling the contact members to respective receptacle member without interfering with the acceptance of the leads.

2. The assembly of claim 1 wherein the radially inward surface of the support member includes a groove, the receptacle members passing through the groove walls so as to be exposed within the groove the flexible printed circuit being mounted along the radially inward surface of the support member and including a pair of through-holes circumventing the receptacle members with the groove.

3. For use with an elongated dental handpiece having first connecting means at its proximal end for coupling the handpiece to a source of electrical power and having second connecting means generally axially spaced therefrom at its distal end for coupling the handpiece to a dental work tool and including an electrical conductor for electrically coupling the first connecting means to an exterior contact region adjacent the distal portion of the handpiece, an improved light source assembly comprising:

an electrically insulative support member adapted to overlie the contact region of the handpiece, a pair of electrically conductive contact member protruding from the radially inward surface of the support member which is proximate to the handpiece so as to contact the contact region thereof, at least one bulb mounted on the radially outward surface of the support member and including first and second electrical leads, a flexible printed circuit for coupling one of the contact members to respective first bulb leads and for coupling the other contact member to respective second bulb leads means for effectively sealing the contact region and contact members from environmental fluids, and means for applying a radial force between the support member and handpiece to insure the electrical connection between the contact member and contact region.

4. The assembly of claim 3 wherein the sealing means includes a pair of resilient surface members interjacent the handpiece and the support member for sealingly engaging the handpiece and support member on the proximal and distal sides of the contact area.

5. The assembly of claim 4 wherein the sealing means includes a pair of O-rings respectively positioned on the proximal and distal sides of the contact area, and the radially inner surface of the support member includes a pair of axially spaced O-rings accepting notches respectively located to the proximal and distal sides of the contact members, the notches and O-rings cooperating to effectively seal the contact region from environmental fluids, the radial force means supplying a sealing force between the O-ring and the support member.

* * * * *